(12) United States Patent
Tesini

(10) Patent No.: US 7,252,507 B2
(45) Date of Patent: Aug. 7, 2007

(54) THERMOPLASTIC WAFER FOR A DENTAL IMPRESSION FOR IDENTIFICATION PURPOSES

(76) Inventor: David A. Tesini, 1 Glen Gery Rd., Shrewsbury, MA (US) 01545

( * ) Notice: Subject to any disclaimer, the term of this patent is extended or adjusted under 35 U.S.C. 154(b) by 635 days.

(21) Appl. No.: 10/098,982

(22) Filed: Mar. 15, 2002

(65) Prior Publication Data
US 2003/0175653 A1    Sep. 18, 2003

(51) Int. Cl.
*A61C 9/00*    (2006.01)
(52) U.S. Cl. .......................................... 433/71; 433/214
(58) Field of Classification Search .................. 433/37, 433/48, 71, 214; 128/861, 862
See application file for complete search history.

(56) References Cited
U.S. PATENT DOCUMENTS

| | | | | |
|---|---|---|---|---|
| 2,183,624 A | * | 12/1939 | Schwartz | |
| 4,324,547 A | * | 4/1982 | Arcan et al. | 433/71 |
| 4,472,140 A | * | 9/1984 | Lustig | 433/38 |
| 4,508,156 A | * | 4/1985 | Banks et al. | 164/35 |
| 4,624,640 A | * | 11/1986 | Tesini | 433/71 |
| 4,869,669 A | * | 9/1989 | Grubbs | 433/140 |
| 5,266,031 A | * | 11/1993 | Marigza | 433/71 |
| 5,503,552 A | * | 4/1996 | Diesso | 433/37 |

* cited by examiner

*Primary Examiner*—Ralph A. Lewis
(74) *Attorney, Agent, or Firm*—Brian M. Dingman, Esq.; Mirick, O'Connell DeMallie & Lougee

(57) ABSTRACT

A method and article for providing identification means, comprising taking an impression of teeth with a thermoplastic wafer of special configuration such that the wafer receives an impression which gives the size, shape and anatomy of each tooth from the occlusal surface to the gum line, and also provides information on tooth position and jaw relationship, to provide maximum information for identification. The wafer also acquires salivary components which, for an indeterminate amount of time, allows for DNA analysis testing or scent dog tracing. The wafer with the impression is then stored for use in case of need, preferably in a container which is sealed so that tampering with the contents can be detected.

19 Claims, 1 Drawing Sheet

THERMOPLASTIC WAFER FOR A DENTAL IMPRESSION FOR IDENTIFICATION PURPOSES

FIELD OF THE INVENTION

This invention relates to a dental impression and saliva-capturing thermoplastic wafer device.

BACKGROUND OF THE INVENTION

In providing means for identification of missing persons, photographs, fingerprints and dental chartings are commonly used. However, in the identification of a human body in which substantial decomposition has occurred, the use of fingerprints is often not possible, and in such cases dental chartings, if available, are often used.

Forensic odontology, the branch of dentistry which is concerned with identification of corpses by dental and oral characteristics, often plays a major role in the identification of missing persons and victims of crime and accidents.

However, if the victim has no dental record, identification by such means is obviously impossible. This is often the case with young children that are missing. A very large percentage of children of pre-school age have never visited a dentist, and a large percentage of those who have visited a dentist merely have an examination for tooth decay or other dental purposes. This record is seldom specific enough to serve as identifying means. Unless some restorative, preventive, or orthodontic treatment has been done that would provide a basis for identification, their dental chartings will have no distinguishable characteristics that might not be shared by many other individuals. No two individuals have the same dental bite characteristics.

In view of the fluoridation of public water supplies, which has reduced the amount of tooth decay in children, it is likely that in the future, even a lower percentage of children will have dental chartings that could be used for identification.

This is a serious problem, since according to the National Center for Missing and Exploited Children close to one million children are reported each year. Over 100,000 attempted abductions by non-family members are reported each year. Of these, 3,000 are successful, some children are returned alive, many are not, and some are never found.

Although bite impressions of wax or other material are often made of a persons teeth, such impressions are used for indicating the location of the upper and lower teeth in relation to each other. Since they usually provide a record only of the occlusal surfaces of the teeth, and no information about the other tooth surfaces, such impressions generally do not give sufficient information for accurate identification. Also, they do not efficiently capture saliva for DNA and scent tracking. Wax bite impression wafers are disclosed in U.S. Pat. No. 4,624,640.

SUMMARY OF THE INVENTION

This invention relates to a method and an article for providing identification, comprising taking an impression of the teeth of a person with a thermoplastic wafer of particular configuration which provides an impression giving the size, shape and anatomy of each tooth from the occlusal surface to the gum line, and provides information on the tooth positions and jaw relationship, to provide maximum identifying information. The wafer can carry an absorbent material that captures saliva and potentially cells from the cheek.

The wafer can be used for taking an impression of a child's teeth either by a dentist, dental auxiliary or a school nurse.

The thermoplastic impression is then stored for use in case of need, in a suitable container, which preferably has means for receiving a security seal to indicate that the contents of the container have not been tampered with. For an indeterminate amount of time the wafer also stores components of saliva.

The bite impression, in addition to tooth characteristics and relationships, also acquires salivary proteins and in cases cells from the cheek that can be used for a DNA sample or FBI trained dogs to trace a scent while searching for a missing child.

BRIEF DESCRIPTION OF THE DRAWINGS

Other objects, features and advantages will occur to those skilled in the art from the following description of the preferred embodiments and the accompanying drawings in which.

DESCRIPTION OF THE ILLUSTRATED EMBODIMENT

Figure 1:
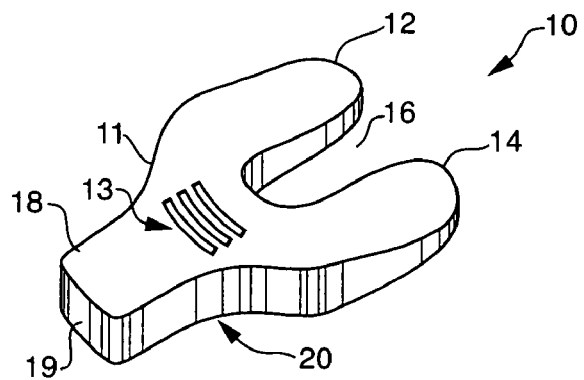
FIG. 1 is a top perspective view of an embodiment of a wafer for making a dental impression for identification purposes embodying features of the invention.

Referring to FIG. 1 of the drawings, there is illustrated a wafer 10 for taking the impression of human teeth, the wafer comprising a unitary molded thermoplastic material defining upper 18 and lower 20 recording surfaces useful for such purpose. The preferred material is a medical grade thermoplastic material.

In a preferred embodiment of the wafer, it is an integral molded member with a plan shape which is generally U-shaped with a pair of posterior segments or lobes 12, 14 joined by an anterior segment 11, and in one embodiment a handle portion 19 extending from the portion 11.

The wafer is shaped to allow it to be inserted into a person's mouth so that the lobes 12, 14 are positioned between the upper and lower molars, and the anterior portion 11 is positioned between the front teeth, that is, the incisors and the canines.

For this purpose the upper and lower layers of each lobe have a thickness such that when the wafer is bitten by a person to form an impression, the layer can receive an impression of not only the biting surface down to the mesial marginal ridge, but also an impression of the inside and outside surfaces of the molars down to the gum line.

The anterior portion 11 is slightly thicker than the posterior lobes, so that a complete impression, including the facial and lingual (front and back) surfaces of the incisors and canines are obtained.

The method of manufacture of a wafer as described is by injection of softened thermoplastic material into a form mold. To accommodate characteristics of the thermoplastic material, an enlarged edge or bead 22 of like or similar material may be used in the design for stability during taking of the impression.

In the illustrated embodiment the lobes 12, 14 have rounded ends, with no wafer material between the lobes in area 16, since such a shape is easier to insert into a child's mouth, and is less threatening to a small child, than wafers which have continuous wafer material between the position of the biting surface of the rear teeth and square ends, which appear to be bigger and may therefore be more frightening to a small child. The absence of material between the lobes also allows the lobes to be folded after softening to alter the posterior thickness if necessary to shorten the wafer, which helps to reduce gagging which sometimes occurs on insertion of a wafer into the mouth.

The projecting handle portion 19 provides a convenient means of handling the wafer during the impression process, particularly when the impression is taken by persons inexperienced in dental methods, such as a school nurse.

The wafer is used to take an impression of teeth in the usual manner, by first warming the wafer, such as in heated water, to a temperature which is hot to the touch but not scalding, inserting the wafer into the mouth far enough that the connecting portion 11 is below the front teeth, and insuring that the lobes 12, 14 are below the upper rear teeth, and having the person whose impression is being taken bite firmly down onto the wafer as far as possible, so that an impression of all of the upper and lower teeth is obtained on the upper and lower thermoplastic surfaces 18 and 20, respectively. Embossed lines 13 can be included to guide correct placement, particularly useful when this is being performed by a non-dental health care provider. Markings 13 would be calculated (and marked) based on the age of the child. They serve as a guide to where the maxillary front incisors would be positioned at the corresponding age.

The wafer may then be removed from the mouth by separating it gently from the teeth. Either just before or just after the impression is taken, the wafer is provided with identifying means, which should include the name, address, and age of the person making the impression. The identifying means may be provided by applying it to a suitable surface on the wafer, or by providing a tag, bearing the identifying information, attached to the wafer.

After the impression is taken and provided with suitable identification means, the wafer should be stored in a small moisture proof container having closure means that includes a security seal, to discourage causal opening of the bag, and to detect tampering.

Figures 2, 3:
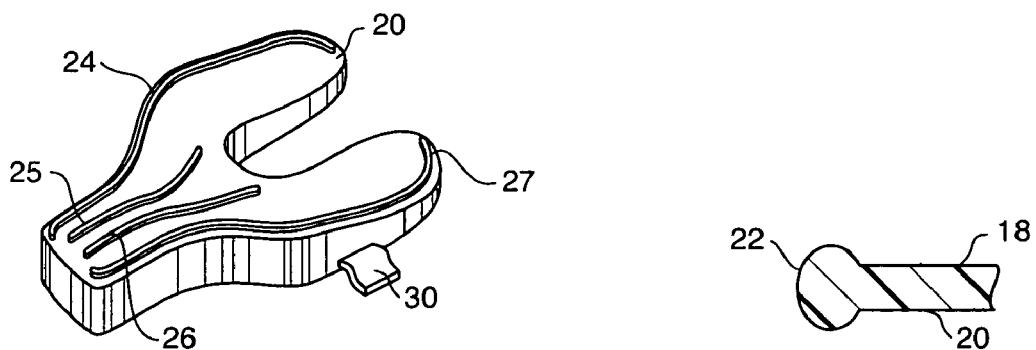
FIG. 2 is a bottom perspective view of a second embodiment.
FIG. 3 is a partial cross-sectional view of an alternative wafer design.

The wafer can be flat, or can have a uniform taper from the front to the rear, providing adequate thickness of the posterior lobes for an impression of the primary and permanent molars substantially to the gum line, and a greater thickness at the anterior portion for an adequate impression of the incisors and canines. The entire wafer can have a bulbous edge of sufficient thickness to add stability and firmness to the wafer and allow placement without difficulty; a wafer which can be made sufficiently soft in warm water to record dental characteristics but remains firm enough to retain its shape. An alternative or additional means to strengthen the wafer is to include one or more strengthening ribs 24–27 on one or both surfaces. FIG. 2 also shows an embodiment of a piece of gauze or similar absorbent material 30 coupled to the wafer along a side so that it contacts a cheek when used. Absorbent material 30 may be sandwiched between two thinner layers of thermoplastic wafer, extending beyond the periphery of the wafer, thereby contacting the cheek when inserted. Material 30 thus preferably captures saliva and cells, both of which are useful for identification.

In the case of a small child, the ideal procedure would be to take an impression on a yearly basis, although such procedure might not be diligently followed by most parents.

The impressed wafer can be scanned or digitized for storage, enhancement, reproducibility and computer comparison purposes.

Therefore a recommended schedule would be to take a first impression of a child's teeth at about age 3, after all 20 primary teeth have erupted, a second impression at about age 6½–7, after the four mandibular (lower) incisors have erupted, a third impression at about age 7½–8 after the four maxillary (upper) incisors have erupted, and a fourth impression at about age 12–13 after all permanent teeth (excluding third molars) have erupted.

If dental treatment is provided after the time at which an impression is taken, and the treatment is of a type which will provide positive identification, then subsequent impressions may not be necessary.

Figure 4:
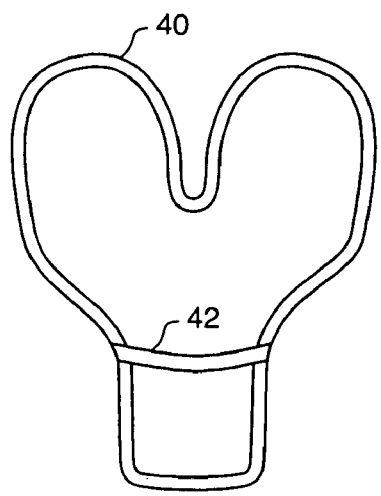
FIG. 4 is a top view of a frame wafer holder useful in the invention.

FIG. 4 shows plastic wafer holding/positioning frame 40. Wafer 10 would fit into frame 40. Anterior positioning flange 42 may be included, positioned to fit between the lip and the upper front teeth, to automatically position wafer 10 correctly. Frame 40 would be useful in situations in which the wafer is placed by a non-health care provider.

Since certain changes obvious to one skilled in the art may be made in the above described embodiments of the invention without departing from the scope thereof, it is intended that all matter contained herein be interpreted in an illustrative and not a limiting sense.

Other embodiments will occur to those skilled in the art and are within the following claims:

What is claimed is:

1. A wafer for taking a simultaneous impression of upper and lower teeth, comprising:
    upper and lower surfaces of impressionable thermoplastic material that softens when warmed,
    the wafer having a pair of laterally spaced portions to receive the impression of the molars and being thick enough to record the shape of the molars from the biting surface substantially to the gum line, and an anterior portion extending between the posterior portions and positioned to receive an impression of the front teeth from the biting edge substantially to the gum line,
    the wafer further including an absorbent material coupled to the wafer along a side of the wafer for capturing cells from the cheek and also for capturing saliva.

2. The wafer of claim 1, which is generally U-shaped in plan with the posterior portion being formed by a pair of spaced legs, the anterior portion connecting the spaced legs.

3. The wafer of claim 2, in which the legs have rounded ends.

4. The wafer of claim 2, further comprising a handle extending from the anterior portion.

5. The wafer of claim 1, wherein the wafer comprises one or more external stiffening ribs.

6. The wafer of claim 1, wherein the wafer is tapered with a thicker anterior portion.

7. The wafer of claim 1, further comprising a removable frame wafer holder for holding the wafer and positioning it in the mouth.

8. The wafer of claim 1, further comprising one or more markings on the surface of the anterior portion of the wafer to assist in aligning the wafer with the teeth.

9. A wafer for taking a simultaneous impression of upper and lower teeth, comprising:
    upper and lower surfaces of impressionable thermoplastic material that softens when warmed,
    the wafer having a pair of laterally spaced portions to receive the impression of the molars and being thick enough to record the shape of the molars from the biting surface substantially to the gum line, and an anterior portion extending between the posterior portions and positioned to receive an impression of the front teeth from the biting edge substantially to the gum line, wherein at least the laterally spaced portions of the wafer comprise enlarged edges that are thicker than the rest of the laterally spaced portions, to stiffen the wafer when it is softened.

10. The wafer of claim 9, which is generally U-shaped in plan with the posterior portion being formed by a pair of spaced legs, the anterior portion connecting the spaced legs and also defining a projecting handle portion for the user to grasp to place the wafer into and remove the wafer from the mouth.

11. The wafer of claim 10, in which the legs have rounded ends.

12. The wafer of claim 10, further comprising a handle extending from the anterior portion.

13. The wafer of claim 9, wherein the laterally spaced portions of the wafer comprise enlarged edges that are thicker than the rest of the laterally spaced portions, to stiffen the wafer when it is softened.

14. The wafer of claim 9, further comprising a feature along the edge of one or both laterally spaced portions of the wafer for capturing cells from the cheek.

15. The wafer of claim 14, wherein the feature for capturing cells comprises an absorbent material coupled to the wafer, and that also captures saliva.

16. The wafer of claim 9, wherein the wafer is tapered with a thicker anterior portion.

17. The wafer of claim 9, further comprising one or more lines on the surface of the anterior portion of the wafer to assist in aligning the wafer with the teeth.

18. A wafer for taking a simultaneous impression of upper and lower teeth, comprising:

upper and lower surfaces of impressionable thermoplastic material that softens when warmed, the wafer having a pair of laterally spaced portions to receive the impression of the molars and being thick enough to record the shape of the molars from the biting surface substantially to the gum line, and an anterior portion extending between the posterior portions and positioned to receive an impression of the front teeth from the biting edge substantially to the gum line, the wafer further including a feature along a side of the wafer for capturing cells from the cheek, wherein the laterally spaced portions of the wafer comprise enlarged edges that are thicker than the rest of the laterally spaced portions, to stiffen the wafer when it is softened.

19. The wafer of claim 18, wherein the wafer comprises one or more external stiffening ribs.

* * * * *